(12) United States Patent
Hecht et al.

(10) Patent No.: US 7,851,457 B2
(45) Date of Patent: Dec. 14, 2010

(54) β-CYCLODEXTRIN DERIVATIVES

(75) Inventors: Sidney Hecht, Charlottesville, VA (US); Vladimir Karginov, Ashburn, VA (US); Noureddine Fahmi, Charlottesville, VA (US)

(73) Assignee: Innovative Biologics, Inc., Herndon, VA (US)

( * ) Notice: Subject to any disclaimer, the term of this patent is extended or adjusted under 35 U.S.C. 154(b) by 0 days.

(21) Appl. No.: 11/045,423

(22) Filed: Jan. 28, 2005

(65) Prior Publication Data

US 2006/0247208 A1 Nov. 2, 2006

(51) Int. Cl.
*A61K 31/724* (2006.01)
*C08B 37/16* (2006.01)
(52) U.S. Cl. .......................... 514/58; 435/375
(58) Field of Classification Search ........................ None
See application file for complete search history.

(56) References Cited

U.S. PATENT DOCUMENTS

| | | | |
|---|---|---|---|
| 4,247,535 A | 1/1981 | Lewis et al. | |
| 4,258,180 A | 3/1981 | Lewis et al. | |
| 4,537,717 A | 8/1985 | Abbott et al. | |
| 5,250,520 A | 10/1993 | Kurita et al. | |
| 5,585,216 A | 12/1996 | Baur et al. | |
| 5,599,912 A | 2/1997 | Rodell et al. | |
| 5,728,823 A | 3/1998 | Reuscher et al. | |
| 5,739,121 A | 4/1998 | Wiebe et al. | |
| 5,760,017 A | 6/1998 | Djedaini-Pilard et al. | |
| 5,800,602 A | 9/1998 | Baur et al. | |
| 5,821,349 A | 10/1998 | Djedaini-Pilard et al. | |
| 5,834,446 A | 11/1998 | Dow et al. | |
| 5,959,089 A | 9/1999 | Hanessian et al. | |
| 6,042,723 A | 3/2000 | Duval et al. | |
| 6,337,385 B1 | 1/2002 | Muir et al. | |
| 6,444,703 B1 | 9/2002 | Kamoda et al. | |
| 6,632,748 B2 | 10/2003 | Yim et al. | |
| 6,716,827 B1 | 4/2004 | Roselli et al. | |
| 6,858,723 B1 | 2/2005 | Auzely-Velty et al. | |
| 7,169,477 B2 | 1/2007 | Lyu et al. | |
| 2003/0050296 A1 | 3/2003 | Bommer et al. | |
| 2004/0116385 A1 | 6/2004 | Vicente et al. | |
| 2005/0059634 A1 | 3/2005 | Venton et al. | |
| 2006/0199785 A1 | 9/2006 | Fahmi et al. | |
| 2006/0247208 A1 | 11/2006 | Karginov et al. | |
| 2007/0021380 A1 | 1/2007 | Wiebe et al. | |
| 2008/0234182 A1 | 9/2008 | Karginov | |
| 2009/0005343 A1 | 1/2009 | Hecht et al. | |

FOREIGN PATENT DOCUMENTS

| | | |
|---|---|---|
| DE | 2425663 | 12/1975 |
| DE | 3710569 A1 | 3/1987 |
| DE | 4136325 | 5/1993 |
| DE | 19520967 | 12/1996 |
| DE | 19520989 | 12/1996 |
| EP | 0447171 | 9/1991 |
| EP | 1245628 | 10/2002 |
| ES | 2053399 | 7/1994 |
| FR | 2669535 | 5/1992 |
| FR | 2839313 | 11/2003 |
| FR | 2878853 | 6/2006 |
| GB | 2261740 | 5/1993 |
| JP | 49085015 | 8/1974 |
| JP | 50140476 | 11/1975 |
| JP | 51142088 | 12/1976 |
| JP | 52138580 | 11/1977 |
| JP | 53049089 | 5/1978 |
| JP | 03075634 | 3/1991 |
| JP | 06065307 | 3/1994 |
| JP | 06136004 A * | 5/1994 |
| JP | 10060006 | 3/1998 |
| JP | 2005290066 | 10/2005 |
| WO | WO 9422455 A1 * | 10/1994 |
| WO | WO9517191 A1 | 6/1995 |
| WO | WO97/31628 | 9/1997 |
| WO | WO97/49735 | 12/1997 |
| WO | WO9749735 A1 | 12/1997 |
| WO | WO9950307 A1 | 10/1999 |
| WO | WO01/040316 | 6/2001 |
| WO | WO01/083564 | 11/2001 |
| WO | WO01/98370 | 12/2001 |
| WO | WO02/077000 | 10/2002 |
| WO | WO03/093300 | 11/2003 |

(Continued)

OTHER PUBLICATIONS

Tamagaki et al. (Journal of the Chemical Society, Perkin Transacations 2: Physical Organic Chemistry, 1995 vol. 2, pp. 389-393).*

(Continued)

*Primary Examiner*—Robert A Zeman
(74) *Attorney, Agent, or Firm*—DLA Piper LLP (US)

(57) ABSTRACT

The invention provides low molecular weight compounds that block the pore formed by protective antigen and inhibit anthrax toxin action. Structures of the compounds are derivatives of β-cyclodextrin. Per-substituted alkylamino derivates displayed inhibitory activity, and they were protective against anthrax lethal toxin action at low micromolar concentrations. Also, the addition of one of the alkylamino derivatives to the bilayer lipid membrane with multiple PA channels caused a significant decrease in membrane conductance. Thus, the invention also provides methods for protection against anthrax toxicity.

14 Claims, 4 Drawing Sheets

FOREIGN PATENT DOCUMENTS

| WO | WO2004/014959 | 2/2004 |
|---|---|---|
| WO | WO2004/085487 | 10/2004 |
| WO | WO2004/087768 | 10/2004 |
| WO | WO2005/042590 | 4/2005 |
| WO | WO2006/001844 | 1/2006 |
| WO | WO2006/027631 | 3/2006 |
| WO | WO2006/075580 | 7/2006 |

OTHER PUBLICATIONS

Bidan et al. (Biosensors and Bioelectronics, 1994, vol. 9, pp. 219-229).*

Hamelin et al. (Journal of Physical Chemistry, 1995, vol. 99(51), pp. 17877-17885).*

Bondarenko et al. (Analytical Chemistry, 1998 vol. 70 No. 14, pp. 3042-3045).*

Tsujihara et al. (Chemistry Letters, 1978, vol. 12, pp. 1333).*

Ng et al. (Journal of Chromatography A, 2002, vol. 968 pp. 31-40).*

Stoeckel et al. Inclusion complexes of flavonoids into natrual and chemically modified B-cyclodextrans. Colloques- Institut National de la Recherche Agronomique (1995), 69 (Polyphenols 94), 191-192.*

Dixon et al., "Anthrax", N. Engl. J. Med., 341(11):815-826 (1999).

Brossier et al., "Toxins of Bacillus anthracis", Toxicon, 39:1747-1755 (2001).

Petosa et al., "Crystal Structure of the Anthrax Toxin Protective Antigen", Nature, 385:833-838 (1997).

Karginov et al., "Treatment of Anthrax Infection With Combination of Ciproflaxacin and Antibodies to Protective Antigen of Bacillus anthracis", FEMS Immun. Med. Microb., 40:71-74 (2004).

Baer et al., "Improved Preparation of Hexakis(6-deoxy)cyclomaltohexaose and Heptakis(6-deoxy)cyclomaltoheptaose", Carbohydr. Res., 228:307-314 (1992).

Vizitiu et al., "Synthesis of Monofacially Functionalized Cyclodextrins Bearing Amino Pendent Groups", J. Org. Chem., 62:8760-8766 (1997).

Iwata et al., "Manufacture of Cyclodextrin Derivatives", Jpn. Kokai Tokkyo Koho, 9pp., (1989).

Minora et al., "Amino Acid Polymers Containing Cyclodextrin in the Main Chain and their Preparation" Jpn. Kokai Tokkyo Koho 5pp., (1994).

Fukuhara et al., "Synthesis and characterization of the first pair of an unlocked and a locked self-inclusion complex from a permethylated alpha-cyclodextrin derivative", Chem. Letters 32(6):536-537 (2003).

Kurita et al., "Cyclodextrin Derivatives", Jpn. Kokai 7pp (1974).

Karginov et al., "Search for cyclodextrin-based inhibitors of anthrax toxins: synthesis, structural features, and relative activities"; Antimicrobial Agents and Chemotherapy (2006), 50(11),3740-3753.

Wang et al., "Per-6-substituted-per-6-deoxy-β-cyclodextrins Inhibit the Formation of β-Amyloid Peptide Derived Soluble Oligomers"; Journal of Medicinal Chemistry (2004), 47(13),3329 -3333.

Croft et al., "Synthesis of Chemically Modified Cyclodextrins", Tetrahedron, 39(9):1417-1474 (1983).

Castro-Hermida et al., "Treatment With B-Cyclodextrin of Natural Cryptosporidium Parvum Infections in Lambs Under Field Conditions", International Journal for Parasitology, 21:1134-1137 (2001).

Salem et al., "Efficacies of Cyclodextrin-Complexed and Liposome-Encapsulated Clarithromycin Against Mycobacterium Avium Complex Infection in Human Macrophages", International Journal of Pharmaceutics, 250:403-414 (2003).

Karginov et al., "β-Cyclodextrin derivatives that inhibit anthrax lethal toxin"; Bioorganic & Medicinal Chemistry, 14(1), 33-40 (2006).

Hoogenboom et al. "Synthesis of star-shaped poly(.vepsiln.-caprolactone) via 'click' chemistry and 'supramolecular click' chemistry"; Chemical Communications (Cambridge, United Kingdom) (38), 4010-4012 (2006).

Casas-Solvas et al. "Synthesis of Nitrogen-Functionalized β-Cycloaltrins", Journal of Organic Chemistry, 69(25), 8942-8945 (2004).

Kraus et al. "A homologous series of persubstituted cyclodextrin amino acids: The quest for tubular self-assembly", European Journal of Organic Chemistry, (19), 4060-4069 (2004).

Sallas et al. "A practical synthesis of amphiphilic cyclodextrins fully substituted with sugar residues on the primary face", Chemical Communications (Cambridge, United Kingdom) (5), 596-597(2004).

Mourtzis et al. "Influence of Host's Substitution on the Orientation of the Guest: Pseudo-rotaxanes of Charged Cyclodextrins with Methyl Orange in Solution"; Supramolecular Chemistry, 16(8), 587-593 (2004).

Heck et al. "Heptakis-6-(5-methylene-thioureido-5'-methyl-2,2'-bipyridyl)-β-cyclodextrin; synthesis and metal complexation study"; Tetrahedron Letters, 44(8), 1533-1536 (2003).

Heck et al. "New scaffolds for supramolecular chemistry: upper-rim fully tethered 5-methyleneureido-5'-methyl-2,2'-bipyridyl cyclodextrins"; Chemistry—A European Journal, 8(11), 2438-2445(2002).

Reddy et al. "An efficient protocol for the reduction of azidocyclodextrins catalyzed by indium"; Indian Journal of Chemistry, Section B: Organic Chemistry Including Medicinal Chemistry, 41B(3), 645-646 (2002).

Velmurugan et al. "Optimization of the reversed-phase high-performance liquid chromatographic separation of the enantiomers of a cationic chiral drug (tolperisone) on a heptakis(6-azido-6-deoxy) perphenylcarbamated β-cyclodextrin column"; Chromatographia, 56(3/4), 229-232(2002).

Chen et al. "Synthesis and chromatographic properties of a novel chiral stationary phase derived from heptakis(6-azido-6-deoxy-2,3-di-O-phenylcarbamoylated)-β-cyclodextrin immobilized onto amino-functionalized silica gel via multiple urea linkages"; Journal of Chromatography, 950(1-2), 65-74 (2002).

Ng et al. Enantiomer separation of flavor and fragrance compounds by liquid chromatography using novel urea-covalent bonded methylated β-cyclodextrins on silica';Journal of Chromatography, 968(1-2), 31-40 (2002).

Wagner et al. "Heptakis-6-(5-methylene-ureido-5'-methy1-2,2'-bithiazolyl)-cyclomaltoheptaose as a new fluorescent poly-dentate ligand"; Tetrahedron Letters, 42(31), 5207-5209 (2001).

Ravoo et al. "Supramolecular tapes formed by a catanionic cyclodextrin in water"; Chemical Communications (Cambridge, United Kingdom), (9), 827-828 (2001).

Busse et al. "An integrated optical Mach-Zehnder interferometer functionalized by β-cyclodextrin to monitor binding reactions"; Sensors and Actuators, B: Chemical, B80(2), 116-124 (2001).

Fulton et al. "Cyclodextrin-based carbohydrate clusters by amide bond formation" Israel Journal of Chemistry, 40(3-4), 325-333 (2000).

Charbonnier et al. "Heptakis-6-(5-methylene-ureido-5'-methyl-2,2'-bipyridinyl)-cyclomaltoheptaose as a new fluorescent lanthanide polydentate ligand"; Tetrahedron Letters, 40(21), 4047-4050 (1999).

Kraus et al. "Novel amphiphilic cyclodextrins: per[6-deoxy-6-(4,5-dicarboxy-1,2,3-triazol-1-yl)-2,3-di-O-methyl] derivatives"; Collection of Czechoslovak Chemical Communications, 63(4), 534-540 (1998).

Borrajo et al. "Derivatized cyclodextrins as peptidomimetics: influence on neurite growth"; Bioorganic & Medicinal Chemistry Letters, 7(9), 1185-1190 (1997).

Jimenez et al. "A mild one-step selective conversion of primary hydroxyl groups into azides in mono- and oligosaccharides"; Carbohydrate Research, 303(3), 367-372 (1997).

Kasselouri et al. "Inclusion capabilities of new amphiphilic cyclodextrins: a steady state fluorescence study, using pyrene"; Journal of Fluorescence, 7(1, Suppl.), 15S-23S (1997).

Gorin et al. "Efficient perfacial derivatization of cyclodextrins at the primary face"; Tetrahedron Letters, 37(27), 4647-4650 (1996).

Ashton et al. "Amino Acid Derivatives of β-Cyclodextrin"; Journal of Organic Chemistry, 61(3), 903-8 (1996).

Alexandre et al. "Scanning force microscopy investigation of amphiphilic cyclodextrin Langmuir-Blodgett films"; Thin Solid Films, 284-285, 765-768 (1996).

Kasselouri et al. "Mixed monolayers of amphiphilic cyclodextrins and phospholipids. I. Miscibility under dynamic conditions of compression"; Journal of Colloid and Interface Science, 180(2), 384-397 (1996).

Guillo et al. "Synthesis of symmetrical cyclodextrin derivatives bearing multiple charges"; Bulletin de la Societe Chimique de France, 132(8), 857-66 (1995).

Coleman et al. "Tailoring cyclodextrins for the construction of large scale molecular assemblies"; NATO ASI Series, Series C: Mathematical and Physical Sciences, 456, 77-97(1995).

Fernandez et al. "Isothiocyanates and cyclic thiocarbamates of α,α'-trehalose, sucrose, and cyclomaltooligosaccharides"; Carbohydrate Research, 268(1), 57-71 (1995).

Kaselouri et al. "Synthesis and self-organizational properties of the per-6-azido-6-deoxy-cyclodextrins"; Polish Journal of Chemistry, 67(11), 1981-5 (1993).

Parrot-Lopez et al. "Self-assembling systems of the amphiphilic cationic per-6-amino-α-cyclodextrin 2,3-di-O-alkyl ethers"; Journal of the American Chemical Society, 114(13), 5479-80 (1992).

Szurmai et al. "Halogen azide displacement to prepare some symmetrically substituted β-cyclodextrin derivatives"; Starch/Staerke, 42(11), 447-9 (1990).

Hattori et al. "Novel HPLC adsorbents by immobilization of modified cyclodextrins"; Journal of Inclusion Phenomena, 5(1), 73-6 (1987).

Hattori et al. "Novel high-performance liquid chromatographic adsorbents prepared by immobilization of modified cyclodextrins"; Journal of Chromatography, 355(2), 383-91 (1986).

Tsujihara et al. "Synthesis of amino derivatives of cycloheptaamylose having strong antimicrobial activities"; Chemistry Letters, (12), 1333-6 (1978).

Tsujihara et al. "The highly selective sulfonylation of cycloheptaamylose and syntheses of its pure amino derivatives"; Bulletin of the Chemical Society of Japan, 50(6), 1567-71 (1977).

Karginov et al. "Inhibition of S. aureus a-hemolysin and B. anthracis lethal toxin by B-cyclodextrin derivatives" Bioorganic & Medicinal Chemistry, vol. 15, No. 16, pp. 5424-5431 (Jun. 2007).

Gu et al. "Stochastic sensing of organic and analytes by a pore-forming protein containing a molecular adapter" Nature, vol. 398, No. 6729, pp. 686-690 (Apr. 1999).

Nitzan et al. "Structure-Activity Relationship of Porphines for Photoinactivation of Bacteria" Photochemistry and Photobiology, vol. 62, No. 2, pp. 342-347 (1995).

Brown et al. "Anticoccidial activity of crown polyethers", Journal of Medicinal Chemistry, vol. 26, No. 4, pp. 590-592 (1983).

Payne, Dean W. et al. 1994. "Evaluation of a new cytotoxicity assay for *Clostridium perfringens* type D epsilon toxin." FEMS Microbiol Lett. 116:161-167.

Stansfield et al. "De novo design of peptidomimetic inhibitors of HCV NS3 protease,"Abstracts of Papers American Chemical Society, vol. 220, Part 1, page MEDI 16 (2000).

Petit, Laetitia et al. 1997. "*Clostridium perfringens* epsilon-toxin acts on MDCK cells by forming a large membrane complex." J Bacteriol. 179(20):6480-6487.

Rostovtseva, Tatiana K. et al. 2002. "Partitioning of Differently Sized poly(ethylene glycol)s into OmpF Porin." Biophysical Jounrla. 82:160-169.

Montal et al. "Formation Biomolecular Membranes from Lipid Monolayers and a Study of Their Electrical Properties" Proc. Nat. Acad. Sci. USA vol. 69, No. 12, Dec. 1972, pp. 3561-3566.

Bezrukov et al. "Probing alamethicin channels with water-soluble polymers effect on conductance of channel states" Biophys. J. vol. 64, Jan. 1993, pp. 16-25.

Benson Ericka L. et al. 1998. "Identification of Residues Lining the Anthrax Protective Antigen Channel." Biochemistry. 37: 3941-3948.

Collier R. John et al. 2003. "Anthrax Toxin." Annu Rev Cell Dev Biol. 19:45-70.

Davis Mark E. et al. 2004. "Cyclodextrin-based pharmaceutics: past, present and future." Nat Rev. 3:1023-1035.

Fukuhara, Gaku et al. 2003. "Synthesis and Characterization of the First Pair of an Unlocked and a Locked Self-inclusion Complex fro ma Permethylated α-Cyclodextrin Derivative". Chemistry Letters. 32(6):536-537.

Hambrook Joy L. et al. 1995. "Morphological alterations in MDCK cells induced by exposure to *Clostridium perfringens* epsilon-toxin." Biochem Soc Trans. 23(1): 44S.

Karginov, Vladimir A. et al. 2005. "Blocking anthrax lethal toxin at the protective antigen channel by using structure-inspired drug design." Proc Natl Acad Sci. 102(42): 15075-15080.

Lindsay, Christopher D. 1996. "Assessment of aspects of the toxicity of *Clostridium perfringens* epsilon-toxin using the MDCK cell line." Hum Exp Toxicol. 15: 904-908.

Moayeri, Mahtab et al. 2004. "The roles of anthrax toxin in pathogenesis." Curr Opin Microbiol. 7:19-24.

Nagahama, Masahiro et al. 1996. "Membrane-damaging action of *Clostridium perfringens* alpha-toxin on phospholipid liposomes." Biochim Biophys Acta. 1280(1):120-126.

Nagahama, Masahiro et al. 2006. "Oligomerization of *Clostridium perfringens* epsilon-toxin is dependent upon membrane fluidity in liposomes." Biochemistry. 45(1):296-302.

Lozitsky et al. "Antiherpetic and Anti-Influenza Activity of Aza-Crown Ethers", Antiviral Research vol. 70, No. 1, p. A49 (abstract).

Hamelin et al., Journal of Physical Chemistry, 1995, 99(51):17877-17885.

Stoecket et al., "Inclusion complexes of flavanoids into naturally and chemically modified β-cyclodextrans"; Colloques—Instut. National de la Recherche Agronomique, 1005 69(94): 191-192.

Uekama, et al., "Cyclodextrin Drug Carrier Systems", Chem. Rev. 1998, 98, 2045-2076.

Athanassiou, et al, "Antimicrobial activity of beta-lactam antibiotics against clinical pathogens after molecular inclusion in several cyclodextrins. A novel approach to bacterial resistance", J Pharm. Pharmacol. Mar. 2003, 55(3):291-300.

* cited by examiner

IC$_{50}$:
1. Am$\beta$CD     15.9 ± 3.5 μM
2. EtAm$\beta$CD     4.4 ± 1.4 μM
3. PrAm$\beta$CD     5.0 ± 1.0 μM
4. BuAm$\beta$CD     8.1 ± 2.0 μM

β-CYCLODEXTRIN DERIVATIVES

This work was supported by grant 1R43AI052894-01 from the National Institute of Allergy and Infectious Diseases. The government has certain rights in this invention.

BACKGROUND OF THE INVENTION

1. Field of the Invention

The invention relates to protection against Anthrax-mediated biotoxicity.

2. Summary of the Related Art

*Bacillus anthracis* is one of the most dangerous potential biological weapons. Currently, there is no effective treatment for inhalational anthrax, beyond the administration of antibiotics shortly after exposure. Time delay reduces the effectiveness of antibiotic treatment. Dixon et al., *Anthrax. N. Engl. J. Med.*: 341, 815-826 (1999) teaches that major factors playing a role in anthrax infection are the cytotoxic effect of anthrax toxin, and bacteremia leading to oxygen and nutritional substance deprivation, accumulation of various bacterial and host toxic products with eventual organ failure and death.

Brossier et al., *Toxicon*. 39: 1747-1755 (2001) teaches that the two anthrax toxins are formed by three different proteins: protective antigen (PA) which either combines with lethal factor (LF) to form lethal toxin (LeTx), or with edema factor (EF) to form edema toxin (EdTx). LF and EF are enzymes targeting substrates within the cytosol, and PA facilitates their transport across the cell membrane forming a heptameric pore. PA assembles into a ring-shaped heptamer with a negatively charged lumen and exposes a hydrophobic surface for binding of LF and EF. Petosa et al., *Nature* 385: 833-838 (1997) teaches the three-dimensional structure of the PA pore.

Karginov et al., *FEMS Immun. Med. Microb.* 40: 71-74 (2004) teaches that treatment of *Bacillus anthracis* infected mice with a combination of the antibiotic ciprofloxacin and partially purified antibodies against anthrax protective antigen dramatically increased survival rates in comparison with antibiotic treatment alone.

Although promising, antibodies are less attractive as potential drugs in comparison with low molecular weight compounds, which offer potentially better penetration through membranes and are not sensitive to proteases.

Therefore, there is a need for new safe and efficient treatments to supplement to traditional antibiotic intervention.

BRIEF SUMMARY OF THE INVENTION

The invention provides new safe and efficient treatments to supplement to traditional antibiotic intervention.

In a first aspect, the invention provides low molecular weight compounds designed to block the pore formed by PA, which can inhibit anthrax toxin action. The high-affinity blockers of PA according to the invention are derivatives of beta-cyclodextrin (β-CD), which is a cyclic molecule comprising seven D-glucose units and having sevenfold symmetry, like the PA pore.

In a second aspect, the invention provides methods for inhibiting the toxic effects of *Bacillus anthrasis*. The methods according to this aspect of the invention comprise contacting a cell with a compound according to the first aspect of the invention.

In a third aspect, the invention provides novel methods for making certain derivatives of β-CD.

DETAILED DESCRIPTION OF THE PREFERRED EMBODIMENTS

The invention relates to protection against Anthrax-mediated biotoxicity. The invention provides new safe and efficient treatments to supplement to traditional antibiotic intervention. The references cited herein reflect the level of knowledge in the field and are hereby incorporated by reference in their entirety. In the case of a conflict between the teachings of the cited references and the present specification, any such conflict shall be resolved in favor of the latter.

In a first aspect, the invention provides low molecular weight compounds designed to block the pore formed by PA, which can inhibit anthrax toxin action. The high-affinity blockers of PA according to the invention are preferably derivatives of beta-cyclodextrin (β-CD), which is a cyclic molecule comprising seven D-glucose units and having sevenfold symmetry, like the PA pore. Alternatively, molecules similar to β-CD, cyclic molecules having sevenfold symmetry, like the PA pore may be used. The outside diameter of β-CD—15.3 Å—is comparable with the diameter of the PA channel lumen, which is 20-35 Å according to X-ray analysis data, and about 12 Å at its most narrow point according to the measurement of current flow through the channel. Alternative cyclic molecules should be of similar size.

Preferred derivatives of β-CD include hepta-6-alkylamino derivatives of β-cyclodextrin. β-CD substituted with positively charged groups of various sizes because the lumen of the PA pore is mostly negatively charged. Also, the positively charged groups might alter the local pH inside the lumen, inhibiting the conformational change required for the formation of the transmembrane channel.

Preferred compounds have the formula wherein $R_2$ is H, OH, OAc, OMe, or $O(CH_2CH_2O)_n$; $R_3$ is H, OH, OAc, OMe, $OSO_3Na$, or $NH_2$; and $R_6$ is H, $NH_2$, $SCH_2CH_2NH_2$, $SCH_2CH_2CH_2NH_2$, $SCH_2CH_2CH_2CH_2NH_2$, I, $N_3$, SH, lower alkyl, S-alkylguanidyl, O-alkylguanidyl, S-aminoalkyl, O-aminoalkyl, aminoalkyl, aralkyl, aryl, heterocyclic ring(s), or $OSO_3Na$. Most preferably, $R_6$ is H, $NH_2$, $SCH_2CH_2NH_2$, $SCH_2CH_2CH_2NH_2$, or $SCH_2CH_2CH_2CH_2NH_2$.

For purposes of the invention, the term "lower alkyl" means an alkyl group from 1 to 7 carbon atoms. The terms "alkyl" and "aryl" include alkyl or aryl groups which may be substituted or unsubstituted. Preferred substitutions include, without limitation, substitution with nitrogen containing moieties, including amino groups, which may be mono or disubstituted, preferably with alkyl or aryl groups. Also, for purposes of the invention the term "alkyl" includes chains of 1-7 atoms with one or more nitrogen atoms and the remainder carbon atoms.

Figure 1:
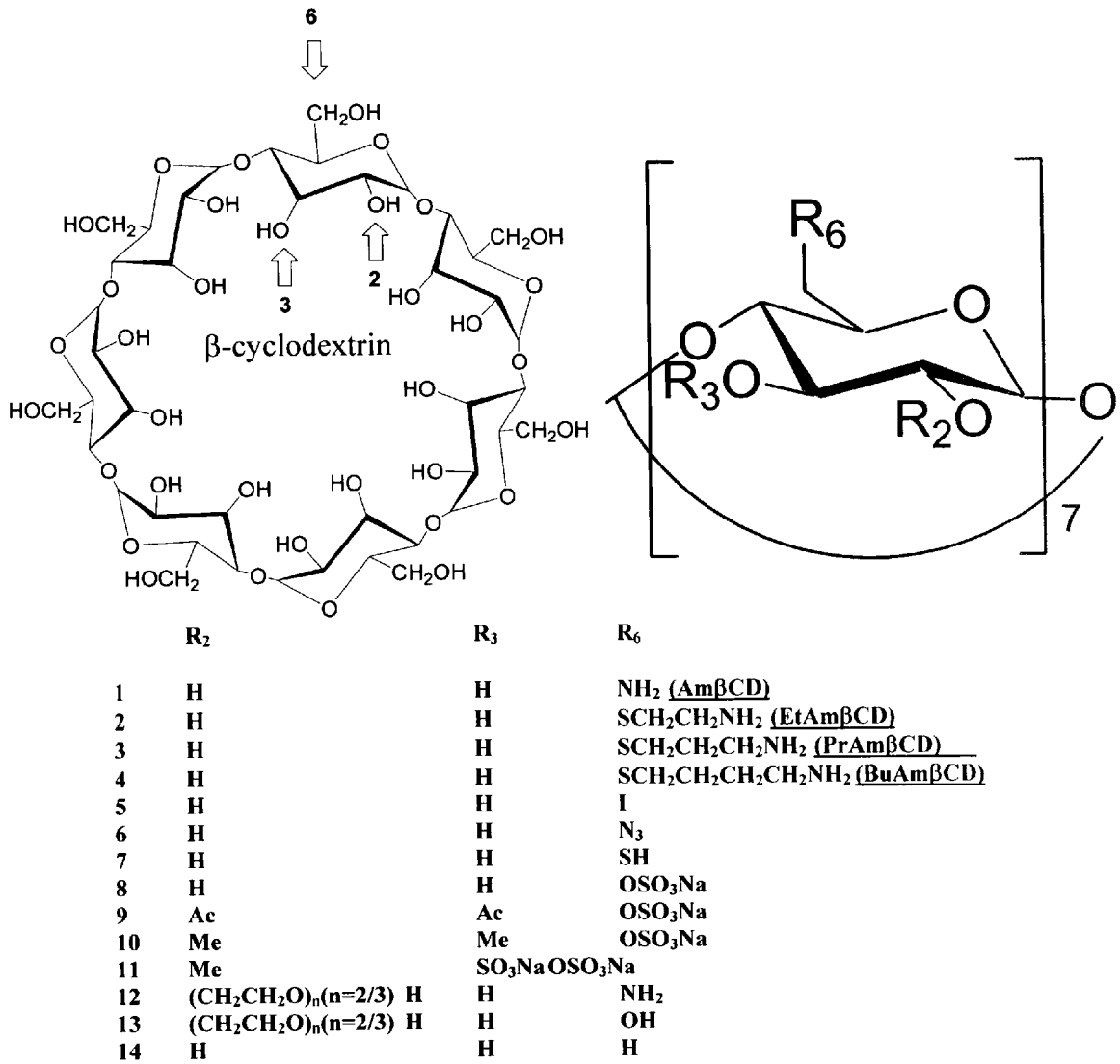
FIG. 1 shows embodiments of compounds according to the invention.

Particularly preferred derivatives of β-CD are shown in FIG. 1.

In a second aspect, the invention provides methods for inhibiting the toxic effects of *Bacillus anthrasis*. The methods according to this aspect of the invention comprise contacting a cell with a compound according to the first aspect of the invention. Preferably, the cell is in a mammal, most preferably in a human.

Figure 2:
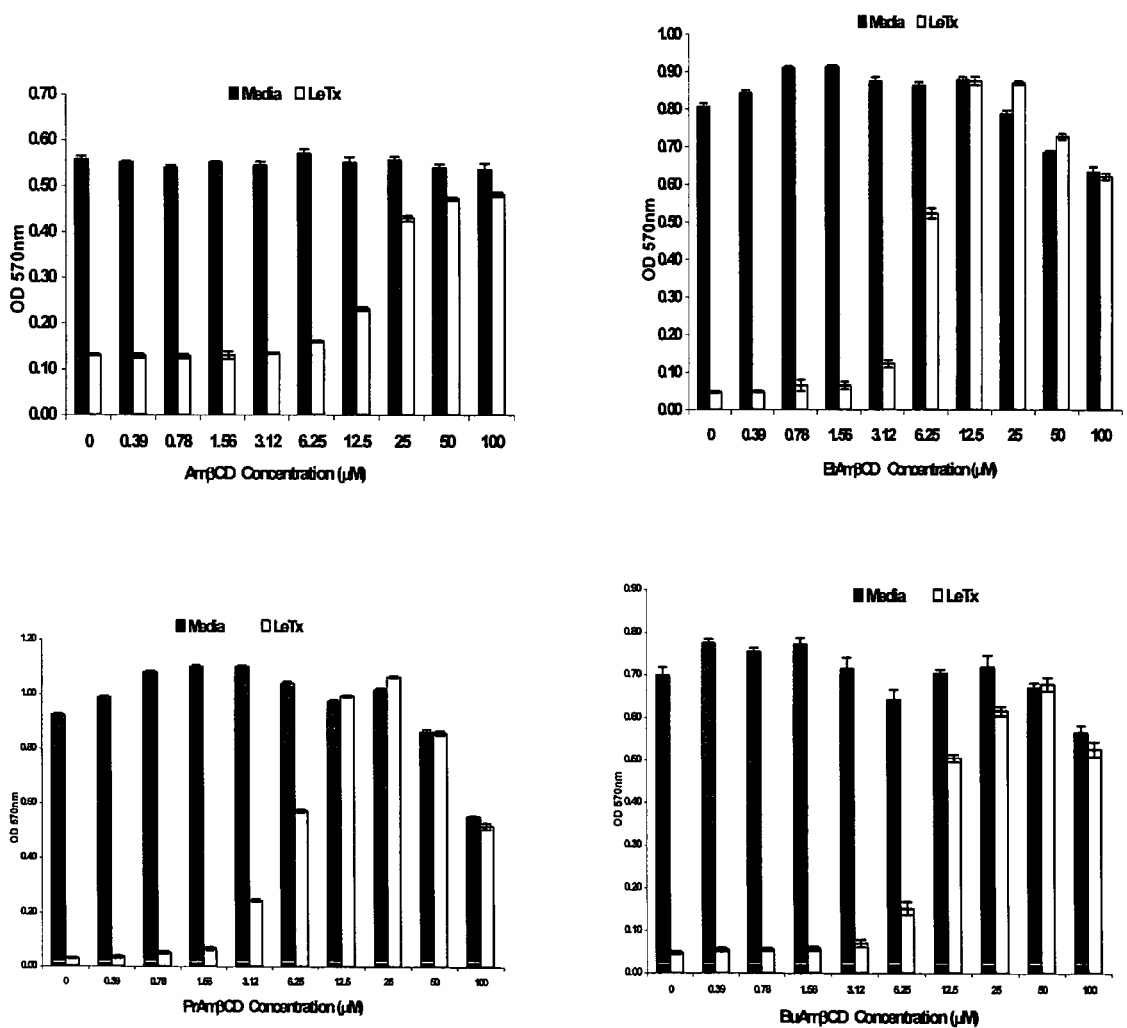
FIG. 2 shows protection of RAW 264.7 cells from LeTx-induced cell death by β-CD derivatives.

The four hepta-6-alkylamino derivatives of β-cyclodextrin suggested by our structure-based evaluation were synthesized. These and some other β-cyclodextrin derivatives synthesized by us or obtained elsewhere (FIG. 2) were tested for their ability to inhibit cytotoxic effect of LeTx on mouse macrophage-like cells RAW 264.7.

Figure 3:
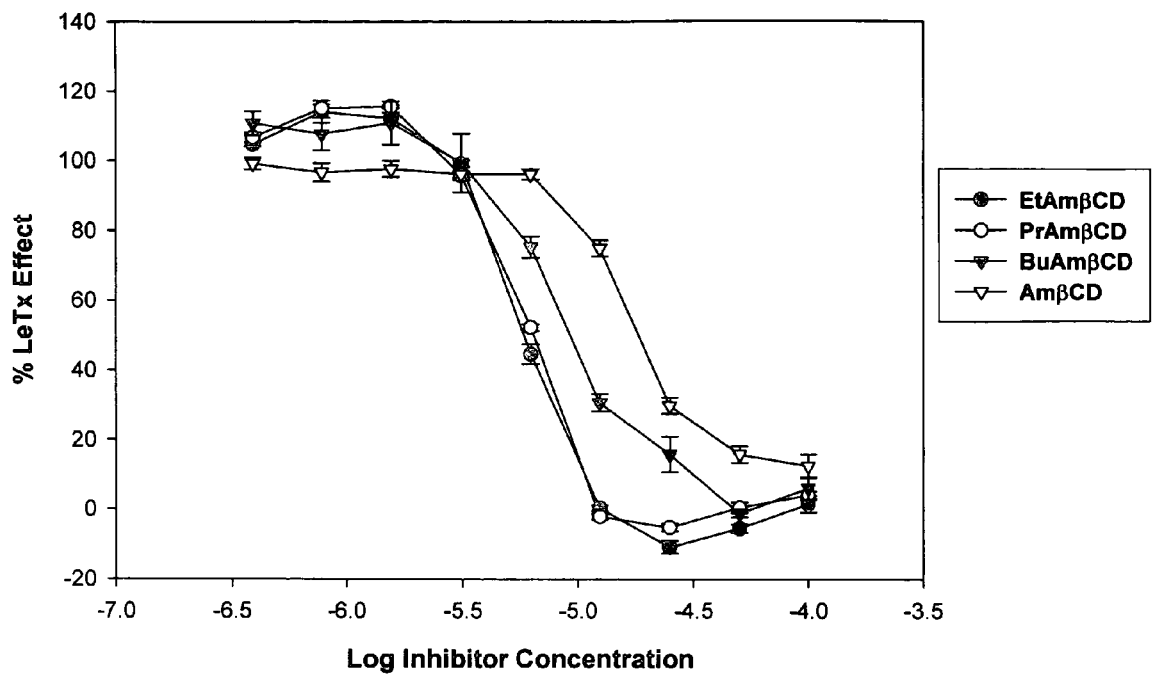
FIG. 3 shows inhibition of cytopathic effect of LeTx expressed as percentage of the LeTx effect induced in cells not treated with inhibitor.

Surprisingly, only the alkylamino derivatives originally suggested based on structure-based design, displayed inhibitory activity, and they were protective against LeTx action at low micromolar concentrations (FIG. 3). These experiments also showed that the compounds were not toxic to RAW 264.7 cells up to 25 μM concentration, while their $IC_{50}$ were as low as 4.4 μM (FIG. 3). The rest of the compounds presented in FIG. 1 displayed no inhibitory activity at concentrations 100 μM and lower.

Figure 4:
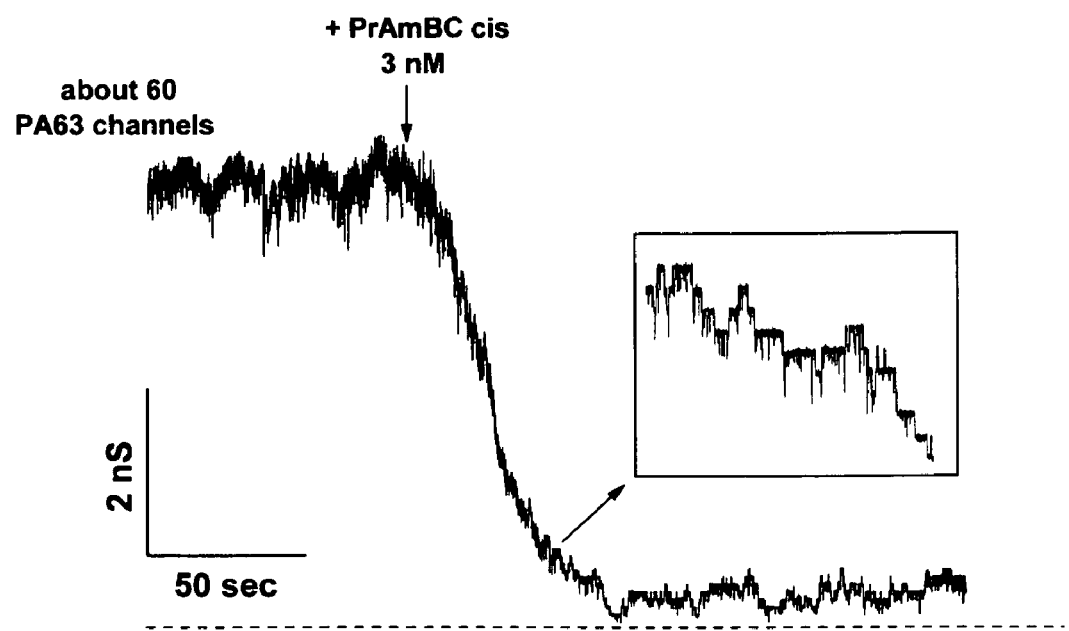
FIG. 4 shows typical tracks of ion conductance for PA channels reconstituted into planar lipid membranes. The downward arrow indicates the addition of PrAmBC to the cis side of the membrane.

One of the alkylamino derivatives—PrAmBC—was tested for the ability to block ion conductance through PA channels reconstituted into planar bilayer lipid membranes. It was demonstrated that the addition of PrAmBC to the bilayer lipid membrane with multiple PA channels (about 60) caused a significant step-like decrease in membrane conductance at 3 nM concentration of the compound (FIG. 4).

Persubstituted β-cyclodextrin derivatives can potentially also be utilized for blocking of other toxins that form heptameric transmembrane channels, such as staphylococcal α-hemolysin. Derivatives of hexameric α-cyclodextrin may also find utility against targets such as *Helicobacter pylori* VacA toxin or hepatitis C virus p7 protein, which form hexameric channels and are considered to be important virulence factors in the pathogenesis of peptic ulcer disease and HCV infection, respectively.

In a third aspect, the invention provides novel methods for making certain derivatives of β-CD. The introduction of an alkylamino group at the primary position of β-cyclodextrins proved to be a challenge. The direct alkylation of per-iodo-β-cyclodextrin with an alcolate nucleophile (derived from an azidoalkanol for example) would pose some problems since the basic alcolate may induce elimination or intramolecular substitutions. Nucleophilic displacement of iodide anions from per-6-iodo-β-cyclodextrins, employing poor nucleophiles or elevated temperatures favors the intramolecular substitution reaction, resulting in the formation of 3,6-anhydro-D-glucopyranose residues within the structure of per-6-iodo-β-cyclodextrin. Taking advantage of the higher nucleophilicity of a sulfur atom over an oxygen atom, we utilized the introduction of a sulfur atom at the primary position of the β-cyclodextrin followed by a selective alkylation of the mercapto group, with a halogenopropionitrile to provide directly a precursor of the target compound 19. In this case, no supplementary protection and deprotection steps are required.

Thus the invention provides an improved method for synthesizing a substituted β-cyclodextrin, wherein the improvement comprises introducing a sulfur atom at the primary position of the β-cyclodextrin followed by a selective alkylation of the mercapto group, with a halogenopropionitrile.

The following examples are intended to illustrate certain particularly preferred embodiments of the invention and are not intended to limit the scope of the invention.

EXAMPLE 1

Synthesis of β-cyclodextrin Derivatives

Reagents. β-cyclodextrin derivatives 1-7 listed in Table 1 were synthesized at Pinnacle Pharmaceuticals, Inc. (Charlottesville, Va.). Compounds 12 and 13 were purchased from Cytrea Ltd (Dublin, Ireland). Sulfo derivatives of β-cyclodextrin 8-11 were kindly provided by Dr. Gyula Vigh (Texas A&M University, College Station, Tex.). β-cyclodextrin 14 was purchased from Sigma (St. Louis, Mo.). Most chemical reagents were purchased from Aldrich Chemicals or Fisher Scientific and used without further purification. Acetonitrile and dichloromethane were distilled from $CaH_2$. DMF was distilled from $CaH_2$ under diminished pressure. Triethylamine was distilled from $P_2O_5$.

Analysis. $^1H$ NMR and $^{13}C$ NMR spectra were recorded on a General Electric QE-300 or a Varian 300 spectrometer. Moisture sensitive reactions were conducted under argon in oven-dried glassware. Analytical thin-layer chromatography was performed on Merk $60F_{254}$ precoated silica gel plates. Visualization was performed by ultraviolet light and/or by staining with phosphomolybdic acid or sulfinuric acid. Flash chromatography was performed using (40-60 μm) silica gel.

Synthesis. Cyclodextrins 2, 3, 4 and 5 were prepared according to standard procedures.

(2-Phthalimidoethyl)isothiouronium hydrobromide (9). A suspension of N-(2-bromoethyl)phthalimide (6) (3.0 g, 11.8 mmol) and thiourea (1.82 g, 23.96 mmol) in absolute EtOH (5.7 mL) was stirred at reflux for 18 h after which the product crystallized. After cooling to room temperature the product was collected by filtration, washing with small amounts of chilled absolute EtOH and dried under vacuum. Compound 9 (4.0 g, quantitative yield) was obtained as colorless crystals; $^1H$ NMR (DMSO-$d_6$) δ 9.04 (brs, 2H), 7.91 (m, 2H); 7.11 (brs, 1H); 3.89 (t, J=5.8 Hz, 2H); 3.52 (t, J=5.8 Hz, 2H).

(3-Phthalimidopropyl)isothiouronium hydrobromide (10). A suspension of N-(3-bromopropyl)phthalimide (7) (3.0 g, 11 mmol) and thiourea (1.7 g, 22.37 mmol) in absolute EtOH (5.3 mL) was stirred at reflux for 18 h after which the product crystallized. After cooling to room temperature the product was collected by filtration, washing with small amounts of chilled absolute EtOH (2×10 mL) and ether (10 mL) and dried under vacuum. Compound 10 (3.95 g, quantitative yield) was obtained as colorless crystals. $^1H$ NMR (DMSO-$d_6$) δ 9.01 (brs, 2H), 7.90 (m, 2H); 3.50 (t, J=6.2 Hz, 2H); 3.20 (t, J=6.6 Hz, 2H); 1.75 (m, 2H).

(4-Phthalimidobutyl)isothiouronium hydrobromide (11). A suspension of N-(4-bromobutyl)phthalimide (8) (1.0 g, 3.5 mmol) and thiourea (540 mg, 7.08 mmol) in absolute EtOH (1.7 mL) was stirred at reflux for 18 h. The product did not crystallize as expected. However, upon cooling to room temperature, the syrupy mixture started crystallizing after a quick shaking and stirring. Ether (4 mL) was added and the mixture stirred for 15 min. before collecting the product by filtration, washing with small amounts of chilled EtOH. Compound 11 (1.22 g, 96%) was obtained as colorless solid; $^1$H NMR (DMSO-$d_6$) δ 9.02 (brs, 2H), 7.89 (m, 4H); 7.13 (brs, 1H); 3.60 (t, J=6.4 Hz, 2H); 3.17 (t, J=6.6 Hz, 2H); 1.67 (m, 4H).

Heptakis (2,3-di-O-acetyl-6-deoxy-6-iodo)cyclomaltoheptaose (14). (See Baer et al., *Carbohydr. Res.* 228: 307 1992). To a solution of per-6-iodo-β-cyclodextrin (2) (1.0 g, 0.52 mmol) in dry pyridine (5 mL was added $Ac_2O$ (7.5 mL) and a catalytic amount of DMAP (6.5 mg, 0.05 mmol). The mixture was stirred at room temperature under argon for 48 h. The reaction was quenched by addition of MeOH (15 mL) and the solvents evaporated under diminished pressure. Coevaporation with small amounts of MeOH (3×4 mL) and toluene (3×4 mL) gave a brown residue, which was purified on a silica gel column (20×3 cm). Elution with a gradient Hexane-EtOAc (1:1 to 1:4) gave compound 14 (1.06 g, 81%) as a colorless solid, which crystallized upon trituration with diethyl ether; $^1$H NMR (CDCl$_3$) δ 5.33 (brt, J=8.4 Hz, 1H); 5.2 (d, J=3.6 Hz, 1H); 4.83 (dd, J=3.9, 9.9 Hz, 1H); 3.58-3.81 (complex m, 4H); 2.09 (s, 3H); 2.05 (s, 3H); mass spectrum (MALDI), calcd. for $C_{70}H_{91}I_7NaO_{42}$ m/z 2514.8 found 2514.9 [M+Na] (100%).

Heptakis [2,3-di-O-acetyl-6-deoxy-6-(2-phthalimidoethyl)-thio]cyclomaltoheptaose (15). To a solution of heptakis (2,3-di-O-acetyl-6-deoxy-6-iodo)cyclomaltoheptaose (14) (0.5 g, 0.2 mmol) and (2-phthalimidoethyl)isothiouronium hydrobromide (9) (0.99 g, 3.0 mmol) in dry DMF (20 mL) was added $Cs_2CO_3$ (1.63 g, 5.0 mmol) and the mixture stirred at room temperature under argon for 48 h. The mixture was poured into ice (40 g) and 0.5 N HCl (200 mL) was added. The aqueous layer was extracted with dichloromethane (3×50 mL). The combined organic phases were washed successively with 0.5 N HCl (200 mL) and brine (100 mL), dried (MgSO$_4$) and evaporated under diminished pressure. The residue was purified on a silica gel column (21×3 cm) eluting with EtOAc to give compound 15 (145 mg, 23%) as a colorless solid. Another fraction (165 mg) was obtained in a slightly impure form. $^1$H NMR (CDCl$_3$) δ 7.73 (m, 2H); 7.62 (m, 2H); 5.25 (t, 1H, J=8.7 Hz); 5.10 (brs, 1H); 4.80 (m, 1H); 4.15 (m, 1H); 3.87 (t, 1H, J=8.4 Hz); 3.63 (m, 2H); 3.03 (m, 2H); 2.64 (m, 2H); 2.05 (s, 3H); 2.01 (s, 3H).

Heptakis [2,3-di-O-acetyl-6-deoxy-6-(3-phthalimidopropyl)-thio]cyclomaltoheptaose (16). To a solution of heptakis (2,3-di-O-acetyl-6-deoxy-6-iodo)cyclomaltoheptaose (14) (250 mg, 0.1 mmol) and (3-phthalimidopropyl)isothiouronium hydrobromide (10) (472 mg, 1.37 mmol) in dry DMF (10 mL) was added $Cs_2CO_3$ (687 mg, 2.11 mmol) and the mixture stirred at room temperature under argon for 68 h. The mixture was poured into ice (50 g) and 0.5 N HCl (100 mL) was added. The aqueous layer was extracted with dichloromethane (3×50 mL). The combined organic phases were washed successively with 0.5 N HCl (100 mL) and brine (100 mL), dried (MgSO$_4$) and evaporated under diminished pressure. The residue was purified on a silica gel column (14×3 cm) eluting with EtOAc to give compound 15 (188 mg, 59%) as a colorless foam; $^1$H-NMR (300 MHz) δ 7.70 (dd, 2H, J=3.0 Hz, J=5.5 Hz); 7.58 (dd, 2H, J=3.1 Hz, J=5.4 Hz); 5.23 (dd, 1H, J=8.3 Hz, J=9.6 Hz); 5.06 (d, 1H, J=3.8 Hz); 4.80 (dd, 1H, J=3.8 Hz, J=9.7 Hz); 4.12 (m, 1H); 3.84 (t, 1H); 3.66 (t, 2H, J=6.9 Hz); 3.03 (m, 2H); 2.60 (m, 2H, J=5.9 Hz, J=12.9 Hz); 2.05 (s, 3H); 2.02 (s, 3H); 1.91 (m, 2H; mass spectrum (MALDI), calcd. for $C_{147}H_{161}N_7NaO_{56}S_7$ m/z 3166.8 found 3166.8 [M+Na] (40%), 3168.8 (100%) and 3167.8 (80%).

Heptakis [2,3-di-O-acetyl-6-deoxy-6-(4-phthalimidobutyl)-thio]cyclomaltoheptaose (17). To a solution of heptakis (2,3-di-O-acetyl-6-deoxy-6-iodo)cyclomaltoheptaose (14) (404 mg, 0.16 mmol) and (4-phthalimidobutyl)isothiouronium hydrobromide (11) (870 mg, 2.42 mmol) in dry DMF (16 mL) was added $Cs_2CO_3$ (1.32 g, 4.04 mmol) and the mixture stirred at room temperature under argon for 48 h. The mixture was poured into ice (50 g) and 0.5 N HCl (200 mL) was added. The aqueous layer was extracted with dichloromethane (3×50 mL). The combined organic phases were washed successively with 0.5 N HCl (100 mL) and brine (100 mL), dried (MgSO$_4$) and evaporated under diminished pressure. The residue was purified on a silica gel column (18×3 cm) eluting with EtOAc to give compound 17 (125 mg, 24%) as a colorless solid. Another fraction (132 mg) was obtained in a slightly impure form. $^1$H-NMR (CDCl$_3$) δ 7.74 (m, 2H); 7.64 (m, 2H); 5.26 (m, 1H); 5.12 (d, 1H, J=3.6 Hz); 4.80 (dd, 1H, J=3.7 Hz, J=9.8 Hz); 4.15 (m, 1H); 3.88 (m, 1H); 3.63 (m, 2H); 3.03 (m, 2H); 2.65 (m, 2H); 2.06 (s, 3H); 2.02 (s, 3H); 1.73 (m, 2H); 1.61 (m, 2H); mass spectrum (MALDI), calcd. for $C_{154}H_{175}N_7NaO_{56}S_7$ m/z 3267.5 found 3267.3 [M+Na] (40%).

Per-6-(2-aminoethylthio)-β-cyclodextrin (18). A mixture of compound 15 (100 mg, 31.92 µmol) and hydrazine monohydrate (1.55 mL, 31.92 mmol) in EtOH-H$_2$O 1:1 (1.5 mL) was stirred at 60° C. for 18 h. The solvents were evaporated under diminished pressure to give a solid, which was suspended in 1N HCl (5 mL) and stirred at rt for 8 h. The insoluble material was filtered and the filtrate diluted with acetone (25 mL) until the product precipitated. The supernatant was removed by centrifugation and the product washed with acetone (4×25 mL) and dried under vacuum. The product 18 (46 mg, 89%) was obtained as a colorless solid. Mass spectrum (MALDI), calcd. for $C_{56}H_{105}N_7O_{28}S_7$ m/z 1548.9 found 1548.8 [M] (100%).

Per-6-(3-aminopropylthio)-β-cyclodextrin (19). A mixture of compound 16 (100 mg, 31.38 µmol) and hydrazine monohydrate (1.54 mL, 31.78 mmol) in EtOH-H$_2$O 1:1 (1.5 mL) was stirred at 60° C. for 16 h. The solvents were evaporated under diminished pressure to give a solid, which was suspended in 1N HCl (5 mL) and stirred at rt for 4 h. The insoluble material was filtered and the filtrate diluted with acetone (25 mL) until the product precipitated. The supernatant was removed by centrifugation and the product washed with acetone (4×25 mL) and dried under vacuum. Compound 19 (53 mg, 85% yield) was obtained as a colorless solid. $^{13}$C-NMR (DMSO-$d_6$) δ 102.09, 84.52, 72.48, 72.23, 71.41, 37.79, 33.03, 29.71, 26.85; mass spectrum (MALDI), calcd. for $C_{63}H_{19}N_7NaO_{28}S_7$ m/z 1668.60 found 1668.82 [M+Na] (100%).

Per-6-(4-aminobutylthio)-α-cyclodextrin (20). A mixture of compound 17 (80 mg, 25.31 µmol) and hydrazine monohydrate (1.22 mL, 25.31 mmol) in EtOH-H$_2$O 1:1 (1.2 mL) was stirred at 60° C. for 24 h. The solvents were evaporated under diminished pressure to give a solid, which was suspended in 1N HCl (5 mL) and stirred at rt for 4 h. The insoluble material was filtered and the filtrate diluted with acetone (25 mL) until the product precipitated. The supernatant was removed by centrifugation and the product washed with acetone (4×25 mL) and dried under vacuum. The product 20 (40 mg, 94%) was obtained as a colorless solid. $^{13}$C-NMR (DMSO-$d_6$) δ 102.05, 84.43, 72.47, 72.22, 71.49, 38.40, 32.85, 32.15, 26.12; mass spectrum (MALDI), calcd. for $C_{70}H_{133}N_7O_{28}S_7$ m/z 1745.3 found 1745.9 [M+Na] (100%).

EXAMPLE 2

Protection of Cells from Cytotoxicity

Recombinant *B. anthracis* lethal factor (rLF), edema factor (rEF), and protective antigen (rPA) were acquired from List Biological Laboratories, Inc. (Campbell, Calif.). Murine RAW 264.7 monocyte-macrophage cell line ATCC TIB-71 was obtained from American Type Culture Collection (Manassas, Va., USA). The cells were cultured in phenol free Dulbecco's Modification of Eagle's Medium/Ham's F-12 50/50 Mix (Mediatech, Inc., Herndon, Va., USA) supplemented with 10% heat-inactivated fetal bovine serum, 100 units/ml:100 μg/ml penicillin-streptomycin, 0.1 mM non-essential amino acids, and 0.5 mM 2-mercaptoethanol at 37° C. in 5% $CO_2$. The cells were harvested using Cellstripper™ from Mediatech, Inc. and then were washed once with media to remove the non-enzymatic dissociation solution. RAW 264.7 cells were plated in 96-well flat-bottomed tissue culture plates from Becton Dickinson (San Jose, Calif., USA) at a concentration of $10^5$ cells/well in the DMEM medium mentioned above and incubated overnight at 37° C. in 5% $CO_2$. RAW 264.7 cells were pre-incubated with different concentrations of tested compounds in DMEM medium for 1 hr at 37° C. in a 5% $CO_2$ atmosphere. Then DMEM medium or LeTx (LF=32 ng/ml; PA=500 ng/ml) in the media were added, and the plate was incubated under the same condition for 4 hrs. Cell viability was estimated using a MTS kit from Promega (Madison, Wis., USA). A μ Quant spectrophotometer from Bio-Tek Instruments, Inc. (Winooski, Vt., USA) was used to obtain $OD_{570}$ readings.

EXAMPLE 3

Inhibition of Ion Conductance

Ion conductance experiments were performed according to Montal and Mueller [14] with modifications [15,16]. PA channels were reconstituted into planar lipid membranes formed from DPhPC; the membrane bathing solution contained 0.1M KCl, 1 mM EDTA at pH 6.6. Ion conductance through PA channels was measured in the presence of PrAmBC.

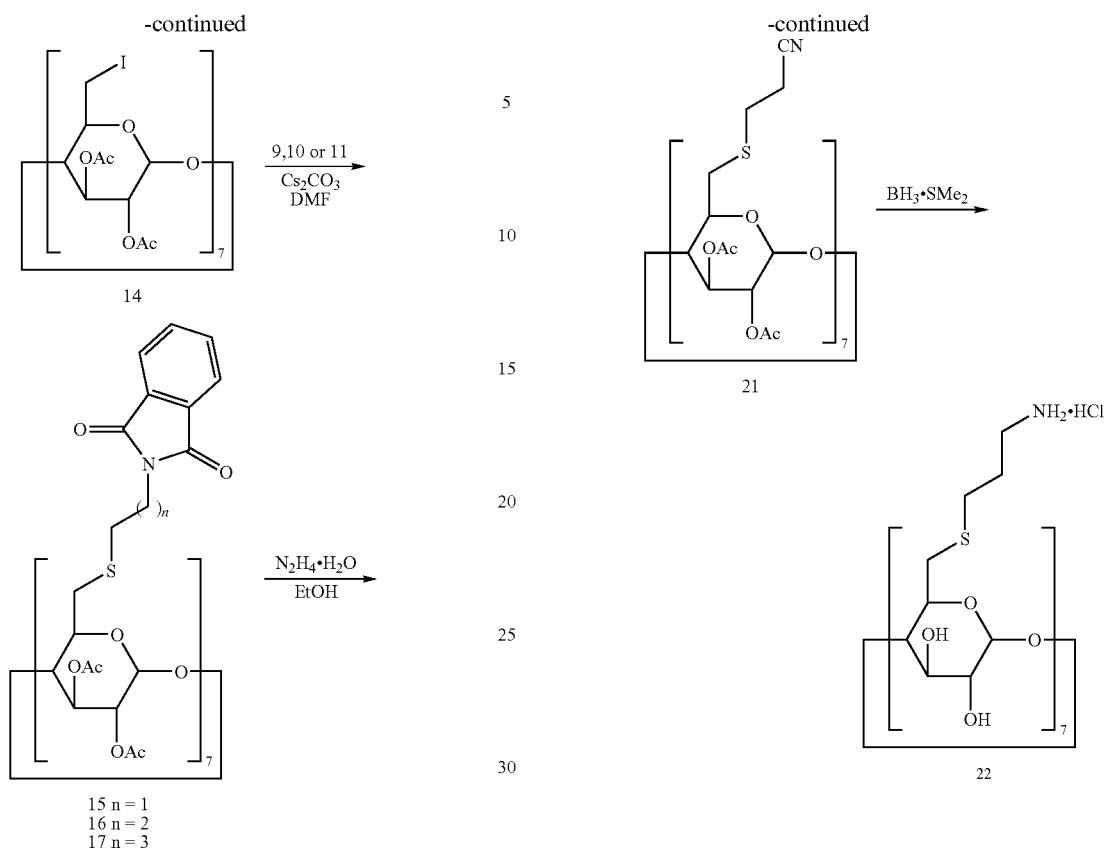

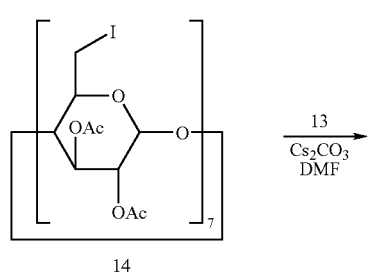

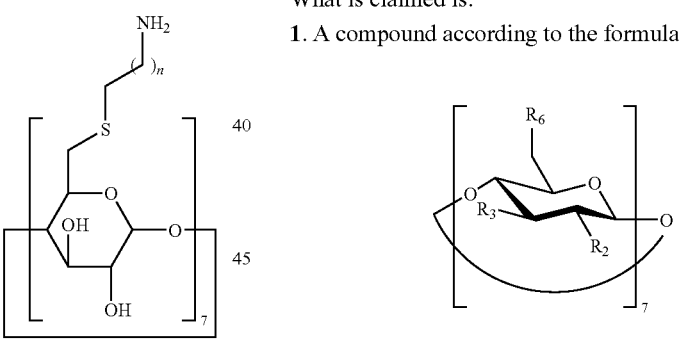

What is claimed is:

1. A compound according to the formula wherein $R_2$ is H; $R_3$ is H, OH, OAc, OMe, $OSO_3Na$, or $NH_2$; and $R_6$ is $NH_2$, $SCH_2CH_2NH_2$, $SCH_2CH_2CH_2NH_2$, $SCH_2CH_2CH_2CH_2NH_2$, I, $N_3$, SH, lower alkyl, S-alkylguanidyl, O-alkylguanidyl, S-aminoalkyl, O-aminoalkyl, aminoalkyl, aralkyl, aryl, heterocyclic ring(s), or $OSO_3Na$.

2. The compound according to claim 1, wherein $R_6$ is $NH_2$, $SCH_2CH_2NH_2$, $SCH_2CH_2CH_2NH_2$, or $SCH_2CH_2CH_2CH_2NH_2$.

3. The compound according to claim 1, wherein $R_6$ is $NH_2$, $N_3$ or aminoalkyl.

4. The compound according to claim 1, wherein $R_6$ is SH, S-alkylguanidyl or S-aminoalkyl.

5. The compound according to claim 1, wherein $R_6$ is O-alkylguanidyl, O-aminoalkyl or $OSO_3Na$.

6. The compound according to claim 1, wherein $R_6$ is lower alkyl, aralkyl, aryl or heterocyclic ring(s).

7. The compound according to claim 1, wherein $R_6$ is I.

8. A compound according to the formula

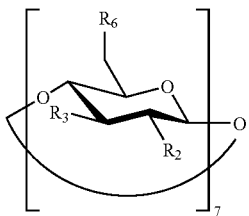

wherein $R_2$ is OMe; $R_3$ is OMe; and $R_6$ is H, $SCH_2CH_2NH_2$, $SCH_2CH_2CH_2NH_2$, $SCH_2CH_2CH_2CH_2NH_2$, I, SH, lower alkyl, S-alkylguanidyl, O-alkylguanidyl, S-aminoalkyl, O-aminoalkyl, aminoalkyl, aralkyl, aryl, or heterocyclic ring(s).

9. The compound according to claim 8, wherein $R_6$ is aminoalkyl.

10. The compound according to claim 8, wherein $R_6$ is SH, lower alkyl, S-alkylguanidyl or S-aminoalkyl.

11. The compound according to claim 8, wherein $R_6$ is O-alkylguanidyl, or O-aminoalkyl.

12. The compound according to claim 8, wherein $R_6$ is lower alkyl, aralkyl, aryl or heterocyclic ring(s).

13. The compound according to claim 8, wherein $R_6$ is $SCH_2CH_2NH_2$, $SCH_2CH_2CH_2NH_2$, or $SCH_2CH_2CH_2CH_2NH_2$.

14. The compound according to claim 8, wherein $R_6$ is I.

* * * * *